US012694510B2

(12) United States Patent
Chatterjee et al.

(10) Patent No.: US 12,694,510 B2
(45) Date of Patent: Jul. 28, 2026

(54) CANCER DETECTION BASED ON FOUR QUADRANT MAPPING AND MATRIX ANALYSIS OF IMAGE DATA

(71) Applicant: THE UNIVERSITY OF CHICAGO, Chicago, IL (US)

(72) Inventors: Aritrick Chatterjee, Chicago, IL (US); Gregory S. Karczmar, Crete, IL (US); Aytekin Oto, Chicago, IL (US); Xiaobing Fan, Darien, IL (US)

(73) Assignee: The University of Chicago, Chicago, IL (US)

( * ) Notice: Subject to any disclaimer, the term of this patent is extended or adjusted under 35 U.S.C. 154(b) by 439 days.

(21) Appl. No.: 17/771,957

(22) PCT Filed: Nov. 11, 2020

(86) PCT No.: PCT/US2020/059997
§ 371 (c)(1),
(2) Date: Apr. 26, 2022

(87) PCT Pub. No.: WO2021/096946
PCT Pub. Date: May 20, 2021

(65) Prior Publication Data
US 2022/0375082 A1 Nov. 24, 2022

Related U.S. Application Data

(60) Provisional application No. 62/935,808, filed on Nov. 15, 2019.

(51) Int. Cl.
*G06T 7/00* (2017.01)
*A61B 5/055* (2006.01)
(Continued)

(52) U.S. Cl.
CPC ............ *G06T 7/0012* (2013.01); *A61B 5/055* (2013.01); *G01R 33/5602* (2013.01);
(Continued)

(58) Field of Classification Search
CPC ......... G06T 7/0012; G06T 2207/10088; G06T 2207/30096; G06V 10/76; G01R 33/5602; G01R 33/56341
See application file for complete search history.

(56) References Cited

U.S. PATENT DOCUMENTS 6,670,812 B1 * 12/2003 Mock ............... G01R 33/56341
324/309
2004/0264752 A1 12/2004 Cline et al.
(Continued)

OTHER PUBLICATIONS

The International Search Report and the Written Opinion issued on Mar. 1, 2021 for international patent application No. PCT/US20/59997; pp. 1-9.

*Primary Examiner* — Qun Shen
(74) *Attorney, Agent, or Firm* — Bell & Manning, LLC

(57) ABSTRACT

A diagnostic system to analyze imaging data includes a memory configured to store hybrid imaging data of a tissue sample. The system also includes a processor operatively coupled to the memory and configured to generate a four quadrant plot based on the hybrid imaging data. Each point in the four quadrant plot corresponds to an image voxel of the tissue sample. The processor is also configured to determine one or more angle values and one or more distance values for image voxels in the four quadrant plot. The processor is further configured to identify one or more characteristics of the tissue sample based at least in part on the one or more angle values and the one or more distance values. The processor is further configured to perform a matrix analysis of the data, which can be used to identify the one or more characteristics of the tissue sample.

14 Claims, 13 Drawing Sheets

(51) Int. Cl.
    *G01R 33/56*        (2006.01)
    *G01R 33/563*     (2006.01)
    *G06V 10/75*       (2022.01)

(52) U.S. Cl.
    CPC ....... *G01R 33/56341* (2013.01); *G06V 10/76*
        (2022.01); *G06T 2207/10088* (2013.01); *G06T*
                               *2207/30096* (2013.01)

(56) References Cited

U.S. PATENT DOCUMENTS

| | | | |
|---|---|---|---|
| 2006/0241375 A1* | 10/2006 | Van Den Brink | ........................... G01R 33/56341 600/410 |
| 2010/0127704 A1 | 5/2010 | Warntjes | |
| 2010/0286053 A1* | 11/2010 | Kuan | ..................... A61K 38/57 514/17.7 |
| 2011/0275926 A1* | 11/2011 | Du | ..................... G01R 33/5635 600/410 |
| 2011/0280457 A1* | 11/2011 | Nielsen | ................. G06T 7/0012 382/128 |
| 2013/0012805 A1* | 1/2013 | Penn | ..................... A61B 5/055 600/411 |
| 2014/0146048 A1 | 5/2014 | Feng et al. | |
| 2016/0022207 A1* | 1/2016 | Roberts | ................. A61B 5/246 600/409 |
| 2017/0337343 A1* | 11/2017 | Kakadiaris | .............. G16Z 99/00 |
| 2019/0265323 A1* | 8/2019 | Lasic | .............. G01R 33/56341 |
| 2020/0101323 A1* | 4/2020 | Ollila | ................... A61N 5/1031 |
| 2020/0278408 A1* | 9/2020 | Sung | ................... G06V 10/764 |
| 2021/0196184 A1* | 7/2021 | Devaraj | ............ G01R 33/5608 |

* cited by examiner

T2-Weighted MRI

Histology

Prostate Quadrant Map

ADC Map (Cancer ROI Marked)

Eigenvalue 3

Eigenvalue 2

Eigenvalue 1

T2-Weighted

Histology

Gleason 4+5

Eigenvalue Map

Fig. 7A

Table: Summary of measured metrics
Mean ± standards deviation reported

| | Prostate Cancer | Benign peripheral zone | Benign transition zone | Benign central zone | Anterior Fibromuscular Stroma |
|---|---|---|---|---|---|
| Sample size | 28 | 20 | 19 | 17 | 14 |
| PQ1 (%) | 3.97 ± 5.86 | 0.76 ± 1.80 | 5.02 ± 7.21 | 2.69 ± 6.34 | 14.18 ± 19.16* |
| PQ2 (%) | 69.86 ± 28.24 | 98.51 ± 3.05* | 86.18 ± 21.75 | 93.38 ± 9.88* | 10.75 ± 19.60* |
| PQ3 (%) | 3.66 ± 8.89 | 0.59 ± 1.84 | 3.07 ± 5.77 | 1.27 ± 2.48 | 7.38 ± 19.28 |
| PQ4 (%) | 22.50 ± 21.27 | 0.13 ± 0.56* | 5.73 ± 15.07* | 2.66 ± 4.05* | 67.68 ± 38.96* |
| Distance | 0.139 ± 0.157 | 0.059 ± 0.28 | 0.033 ± 0.025 | 0.048 ± 0.036 | 0.139 ± 0.157* |
| Angle (°) | 102.5 ± 59.9 | 168.8 ± 8.49* | 138.4 ± 41.1* | 155.0 ± 18.2* | 3.7 ± 46.5* |

*Represents that it is significantly ($p < 0.05$) different from cancer based on ANOVA and post hoc Tukey test*

Fig. 7B

Table: Summary of measured metrics
Mean ± standards deviation reported

| | Gleason score 6 Cancer | Gleason score 7 Cancer | Gleason score 9 Cancer | Spearman Correlation coefficient |
|---|---|---|---|---|
| Sample size | 11 | 14 | 3 | - |
| PQ1 (%) | 0.79 ± 2.62 | 6.83 ± 6.92* | 2.29 ± 1.07 | 0.513⁺ |
| PQ2 (%) | 83.70 ± 23.52 | 66.14 ± 26.29 | 36.47 ± 26.14* | -0.495⁺ |
| PQ3 (%) | 0.00 ± 0.00 | 3.96 ± 7.67 | 15.71 ± 19.86 * | 0.609⁺ |
| PQ4 (%) | 15.51 ± 21.27 | 23.06 ± 20.53 | 45.54 ± 6.38 | 0.388⁺ |
| Distance | 0.237 ± 0.013 | 0.015 ± 0.012 | 0.007 ± 0.003 | -0.545⁺ |
| Angle (°) | 134.2 ± 44.3 | 93.5 ± 53.4 | 29.0 ± 77.6* | 0.532⁺ |

\* Represents that it is significantly ($p < 0.05$) different from Gleason score 6 cancer based on ANOVA and post hoc Tukey test ⁺ *Represents that it is significantly ($p < 0.05$) correlation*

Area Under the Curve

Test Result Variable(s): Predicted probability

| Area | Std. Error[a] | Asymptotic Sig[b] | Asymptotic 95% Confidence Interval | |
|------|------|------|------|------|
| | | | Lower Bound | Upper Bound |
| .893 | .037 | .000 | .822 | .965 | a. Under the nonparametric assumption b. Null hypothesis: true area = 0.5

CANCER DETECTION BASED ON FOUR QUADRANT MAPPING AND MATRIX ANALYSIS OF IMAGE DATA

CROSS-REFERENCE TO RELATED APPLICATION

This application claims priority as a National Stage of International Application No. PCT/US20/59997, filed Nov. 11, 2020, which claims the priority benefit of U.S. Provisional Patent Application No. 62/935,808 filed on Nov. 15, 2019, the entire contents of each of which are incorporated herein by reference.

REFERENCE TO GOVERNMENT RIGHTS

This invention was made with government support under grant number CA172801 awarded by the National Institutes of Health. The government has certain rights in the invention.

BACKGROUND

Cancers can be categorized based on a number of attributes, such as type of cancer, stage of the cancer, and grade of the cancer. The cancer stage refers to how the cancer is behaving at the macro level, and the cancer grade refers to how the cancer cells are behaving on the micro level. As an example, prostate cancer can be graded according to a Gleason Score, which is a system that relies on five distinct patterns of cancerous cells as the cells change from normal cells to tumor cells. A most predominant pattern identified in the cells is assigned a first Gleason grade, and a second most predominant pattern identified in the cells is assigned a second Gleason grade. The first and second Gleason grades are added to determine the Gleason score. The cells with a higher Gleason score (e.g., 8-10) are considered high grade, and have mutated to a point that they do not resemble normal cells. Cells having lower Gleason scores (e.g. 6 or lower) are considered low grade, and cells having a Gleason score of 7 are considered intermediate grade.

SUMMARY

An illustrative diagnostic system to analyze imaging data includes a memory configured to store hybrid imaging data of a tissue sample. The system also includes a processor operatively coupled to the memory and configured to generate a four quadrant plot based on the hybrid imaging data. Each point in the four quadrant plot corresponds to an image voxel of the tissue sample. The processor is also configured to determine one or more angle values and one or more distance values for image voxels in the four quadrant plot. The processor is further configured to identify one or more characteristics of the tissue sample based at least in part on the one or more angle values and the one or more distance values. As discussed in more detail below, the processor is further configured to perform a matrix analysis of the data, which can be used to determine cancer presence.

An illustrative diagnostic method of analyzing imaging data includes storing, in a memory of a computing system, hybrid imaging data of a tissue sample. The method also includes generating, by a processor operatively coupled to the memory, a four quadrant plot based on the hybrid imaging data, where each point in the four quadrant plot corresponds to an image voxel of the tissue sample. The method also includes determining, by the processor, one or more angle values and one or more distance values for image voxels in the four quadrant plot. The method further includes identifying, by the processor, one or more characteristics of the tissue sample based at least in part on the one or more angle values and the one or more distance values.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 7A is a table that includes a summary of measured metrics across prostate cancer, the benign peripheral zone, the benign transition zone, the benign central zone, and anterior fibromuscular stroma in accordance with an illustrative embodiment.

FIG. 7B is a table that includes a summary of measured metrics for Gleason score 6 cancer, Gleason score 7 cancer, and Gleason score 9 cancer, along with the Spearman correlation coefficients in accordance with an illustrative embodiment.

DETAILED DESCRIPTION

Figure 1:
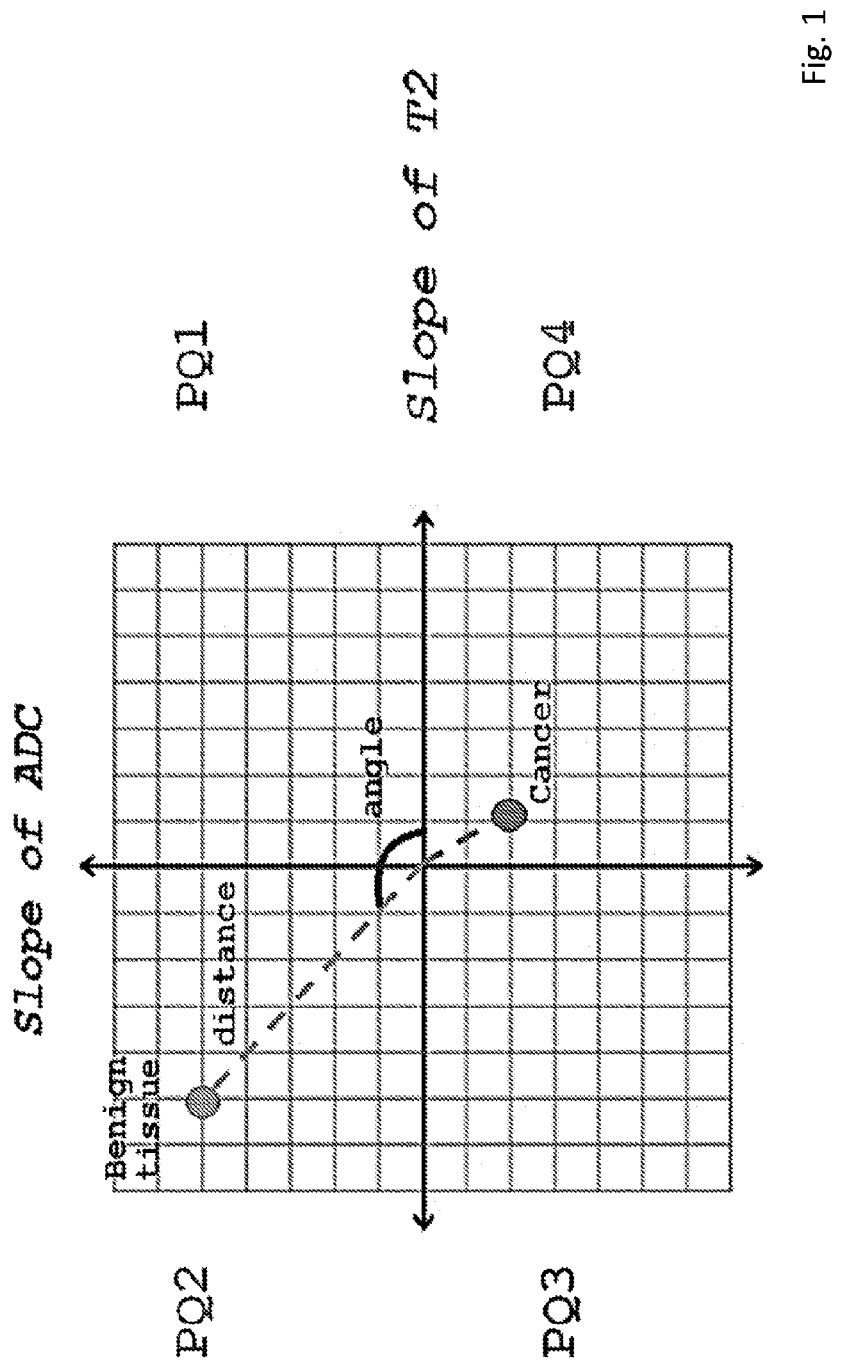
FIG. 1 depicts a 4 quadrant plot, each point in which corresponds to an image voxel of the prostate, in accordance with an illustrative embodiment.

Described herein are systems and methods that improve the analysis of multi-dimensional hybrid magnetic resonance imaging (MRI) data by producing new and effective diagnostic parameters using an innovative method of data analysis. More specifically, the proposed systems and methods provide a new way to screen for prostate cancer by identifying signals that are specific for cancer and that correlate with the Gleason score. The proposed systems and methods utilize 4 quadrant and matrix analysis techniques to enhance the compartmental analysis of hybrid multi-dimensional MRI data, and to provide a virtual pathology of the prostate. The example embodiments described herein are with respect to the prostate and prostate cancer. In alternative embodiments, the described techniques can be applied to other types of cancers that occur in different body parts.

It has been shown that the relationship between the change in apparent diffusion constant as a function of spin echo evolution time, and the change in measured T2 (i.e., transverse relation time) as a function of b-value is a useful diagnostic parameter. As discussed in more detail below, the b-value (or b) is a factor that can be represented in terms of the slope of a line and that reflects the strength and timing of the gradients used to generate diffusion weighed images). Described herein is a newly developed parameter referred to as 'PQ4' that evaluates this interdependence over the whole tumor. As originally developed, PQ4 could not be calculated on a voxel-by-voxel basis and it was therefore not initially possible to make images that represented this property. The present disclosure proposes several new but related methods for measuring and visualizing the PQ4 parameter. These methods are based on vector representations of each image voxel in a 3-dimensional or higher dimensional parameter space. As described in more detail below, the vector representations can be used to help identify prostate cancers and Gleason grade. In addition, this method for analyzing hybrid multi-dimensional MRI data may have applications related to other cancers—especially cancers arising from glandular tissues like the breast, pancreas, etc.

The inventors have developed innovative approaches to analyze Hybrid Multidimensional MRI (HM-MRI) data based on distance and/or angle maps. These techniques are referred to as or quadrant mapping or quadrant analysis, and also involve matrix analysis. The described approaches can be used to identify/diagnose cancer, to monitor cancer, to help determine the effectiveness of cancer treatment, etc. In HM-MRI, T2-weighted imaging and diffusion weighted imaging (DWI) are combined into a single sequence and interdependence of T2 and the apparent diffusion coefficient (ADC) is exploited and modeled to generate novel, quantitative MR features. For example, a matrix of b-values and echo time (TE) values associated with each image voxel can be generated and analyzed.

In conventional diffusion imaging, a series of b values are typically sampled at a single short TE, and conventional T2 mapping typically samples only multiple TE's at b=0. In contrast, the proposed HM-MRI technique samples all matrix elements sampled by conventional diffusion and T2 imaging and in addition, samples many other elements of the matrix. As just one example, HM-MRI can be used to sample a 3×3 matrix of b and TE values associated with each image voxel. Alternatively, other matrix sizes and/or values may be used. Such HM-MRI sampling of the TE/b parameters space allows one to study the interdependence of T2 and ADC, and this new information allows for identification of water signals that are characteristic of cancers. In some embodiments, the change in ADC as a function of echo time (TE) and change in T2 as a function of b value can be measured based on the slope of ADC(TE) and slope of T2($b$), using all of the matrix elements. A larger hybrid matrix can also be imaged to obtain exponential fits, and the decay constants can be used for a 4 Quadrant Analysis (4QA).

FIG. 1 depicts a 4 quadrant plot, each point in which corresponds to an image voxel of the prostate, in accordance with an illustrative embodiment. As shown, the 4 quadrants are PQ1) (0°-90°, PQ2) (90°-180°), PQ3 (180°-270°, and PQ4) (270°-360°. Using the quadrant diagram (or a representation thereof), angle plots (or other calculations) can be used to describe each point in any of the quadrants. FIG. 1 depicts an angle (relative to the x-axis) of a point in PQ2, as represented at the end of the dashed line in PQ2. The quadrant diagram can also be used to generate distance plots for each point in any of the quadrants. In FIG. 1, the dashed line in PQ2 represents a distance (from the origin) to the point in PQ2, and the dashed line in PQ4 represents a distance (from the origin) to a point in PQ4. In one embodiment, points on the quadrant plot can be represented using polar coordinates. Alternatively, Cartesian or other coordinate systems may be used.

Referring still to FIG. 1, y=slope of ADC(TE), and x=slope of T2(b-value) in the quadrant plot. Additionally, as discussed above, each voxel is associated with a distance from the origin (where ADC and T2 have not changed for the hybrid MRI matrix on changing imaging parameters b and TE) and an angle. Results show that benign tissue lies in quadrant 2 (PQ2) where both the slope of ADC and T2 are negative, or these values are reduced at higher TE and b-values. A distinctive property of aggressive cancers is that they have been found to include a higher percentage of voxels in the 4th quadrant (PQ4), where even though ADC is reduced with increasing TE, T2 increases at a higher b-value.

In an illustrative embodiment, the proposed system can include and/or be in communication with a computing system that includes a memory, processor, user interface, transceiver, and any other computing components. Any of the operations described herein may be performed by the computing system. The operations can be stored as computer-readable instructions on a computer-readable medium such as the computer memory. Upon execution by the processor, the computer-readable instructions are executed as described herein. As an example, FIG. 2 is a block diagram of a system for performing quadrant and matrix analysis of hybrid imaging data in accordance with an illustrative embodiment.

Figure 2:
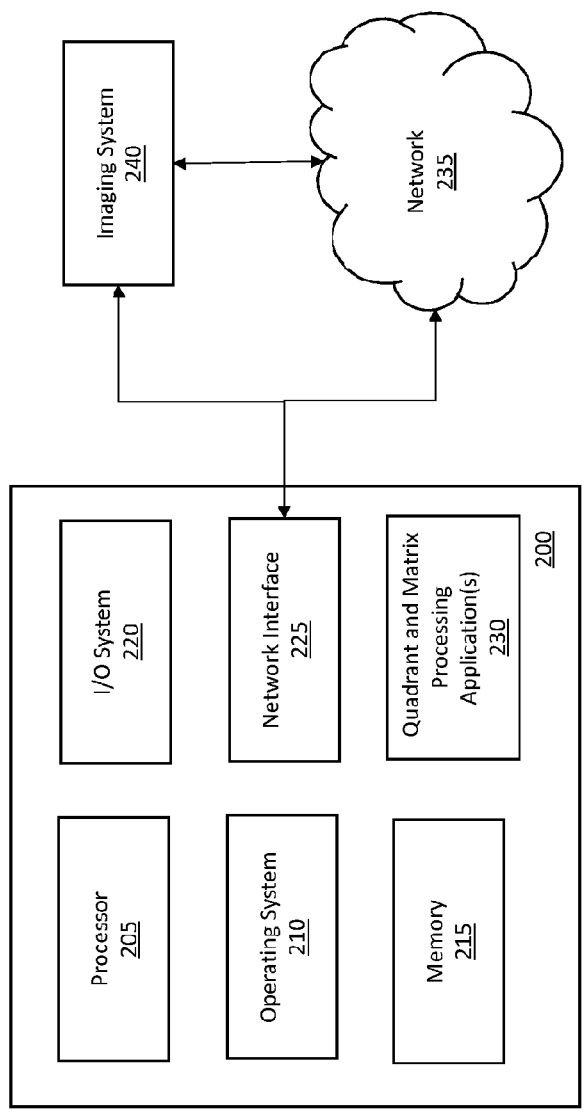
FIG. 2 is a block diagram of a system for performing quadrant and matrix analysis of hybrid imaging data in accordance with an illustrative embodiment.

FIG. 2 depicts a computing device 200 in communication with a network 235 and an imaging system 240. The imaging system 240 can be an MRI system, or any other type of imaging system that is able to provide hybrid image data to the computing device 200. The computing device 200 includes a processor 205, an operating system 210, a memory 215, an input/output (I/O) system 220, a network interface 225, and quadrant and matrix processing application(s) 230. In alternative embodiments, the computing device 200 may include fewer, additional, and/or different components. The components of the computing device 200 communicate with one another via one or more buses or any other interconnect system. The computing device 200 can be any type of networked computing device such as a laptop computer, desktop computer, smart phone, tablet, workstation, server, etc.

The processor 205 can be in electrical communication with and used to control any of the system components described herein. The processor 205 can be any type of computer processor known in the art, and can include a plurality of processors and/or a plurality of processing cores. The processor 205 can include a controller, a microcontroller, an audio processor, a graphics processing unit, a hardware accelerator, a digital signal processor, etc. Additionally, the processor 205 may be implemented as a complex instruction set computer processor, a reduced instruction set computer processor, an x86 instruction set computer processor, etc. The processor 205 is used to run the operating system 210, which can be any type of operating system.

The operating system 210 is stored in the memory 215, which is also used to store programs, user data, network and communications data, peripheral component data, the quadrant and matrix processing application(s) 230, and other operating instructions. The memory 215 can be one or more memory systems that include various types of computer memory such as flash memory, random access memory (RAM), dynamic (RAM), static (RAM), a universal serial bus (USB) drive, an optical disk drive, a tape drive, an internal storage device, a non-volatile storage device, a hard disk drive (HDD), a volatile storage device, etc.

The I/O system 220 is the framework which enables users and peripheral devices to interact with the computing device 200. The I/O system 220 can include a mouse, a keyboard, one or more displays, a speaker, a microphone, etc. that allow the user to interact with and control the computing device 200. The I/O system 220 also includes circuitry and a bus structure to interface with peripheral computing devices such as power sources, the imaging system 240, USB devices, data acquisition cards, peripheral component interconnect express (PCIe) devices, serial advanced technology attachment (SATA) devices, high definition multimedia interface (HDMI) devices, proprietary connection devices, etc.

The network interface 225 includes transceiver circuitry that allows the computing device to transmit and receive data to/from other devices such as the imaging system 240, remote computing systems, servers, websites, etc. The network interface 225 enables communication through the network 235, which can be one or more communication networks. The network 235 can include a cable network, a fiber network, a cellular network, a wi-fi network, a landline telephone network, a microwave network, a satellite network, etc. The network interface 225 also includes circuitry to allow device-to-device communication such as Bluetooth® communication.

The quadrant and matrix processing application(s) 230 can include software and algorithms in the form of computer-readable instructions which, upon execution by the processor 205, performs any of the various operations described herein such as processing data received from the imaging system 240, performing matrix analyses, generating quadrant plots, analyzing the quadrant plots, solving equations, determining Gleason scores, identifying cancerous areas based on the quadrant plots, identifying non-cancerous areas, etc. The quadrant and matrix processing application(s) 230 can utilize the processor 205 and/or the memory 215 as discussed above. In an alternative implementation, the quadrant and matrix processing application(s) 230 can be remote or independent from the computing device 200, but in communication therewith.

Figure 3:
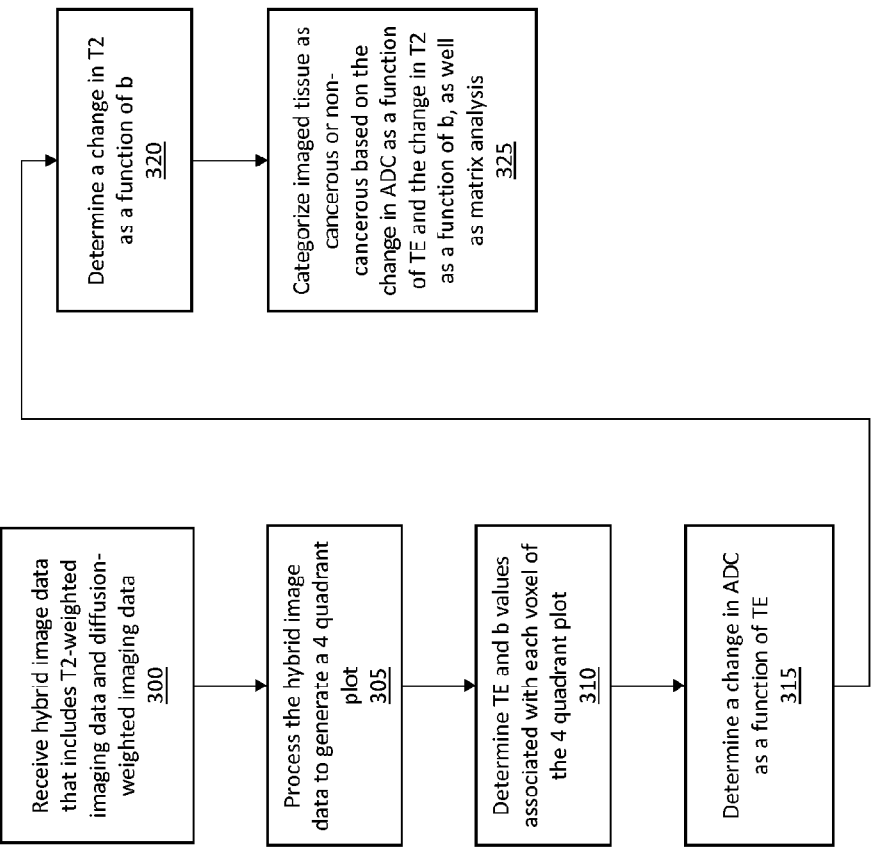
FIG. 3 is a flow diagram depicting operations performed by a system for performing four quadrant and matrix analysis of hybrid imaging data in accordance with an illustrative embodiment

FIG. 3 is a flow diagram depicting operations performed by a system for performing four quadrant and matrix analysis of hybrid imaging data in accordance with an illustrative embodiment. In alternative embodiments, fewer, additional, and/or different operations may be performed. Additionally, the use of a flow diagram is not meant to be limiting with respect to the order of operations performed. In an operation 300, the system receives hybrid image data that includes T2-weighted imaging data and diffusion-weighted imaging data. In an illustrative embodiment, the imaging data is received from an MRI machine, and is thus hybrid MRI imaging data. Alternatively, a different type of imaging system may be used to obtain the imaging data.

In an operation 305, the system processes the received image data to generate a four quadrant plot. In an illustrative embodiment, the system can perform a matrix analysis on the received hybrid image data to determine the eigenvalues of a hybrid matrix associated with each image voxel. For each image voxel, system combines a plurality (e.g., 3, etc.) of eigenvalues and maps a linear combination of the eigenvalues. In another illustrative embodiment, each point in the four quadrant plot corresponds to an image voxel of the received image data, and each image voxel is associated with a tissue region. In an operation 310, the system determines TE and b values associated with each voxel of the four quadrant plot. In an operation 315, the system uses the plot (or equivalent data) to determine a change in ADC as a function of TE. In an operation 320, the system uses the plot (or equivalent data) to determine a change in T2 as a function of b. In an operation 325, the system categorizes the imaged tissue as cancerous or non-cancerous based on the change in ADC as a function of TE and the change in T2 as a function of b. The categorization can also be based at least in part on matrix analysis as discussed herein.

In some embodiments, to further increase the diagnostic accuracy of the four quadrant analysis, additional dimensions can be added to the hybrid data analysis. To do this, multi-dimensional fits to the hybrid 'b' vs. 'TE' matrix can be used. For example, multi-exponential functions either along the 'b' dimension, or the 'TE' dimension—or along diagonals in a hybrid matrix associated with each image voxel can be used. This will allow 3-dimensional and higher dimensional maps that include the different components of multi-dimensional fits. Additionally, vectors or tensors can be analyzed based on magnitude, angles, and other properties to obtain diagnostically useful information.

Figure 4B:
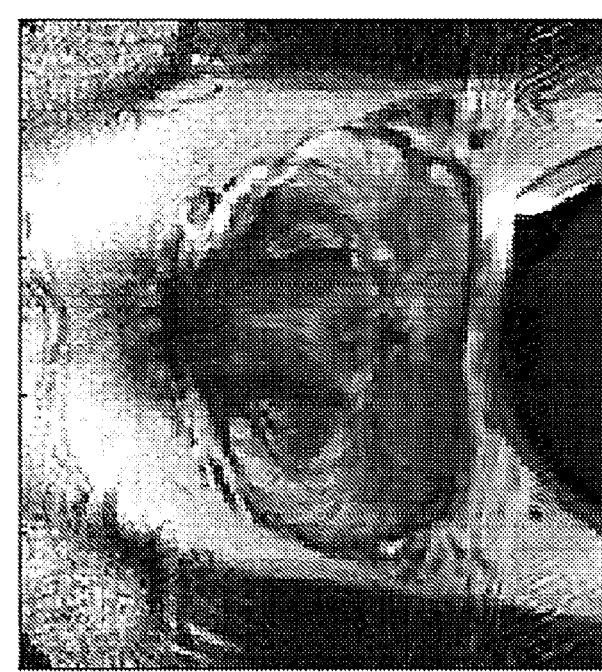
FIG. 4B depicts a T2-weighted MRI image of the prostate of the first patient in accordance with an illustrative embodiment.
Figure 4A:
FIG. 4A depicts a histological view of the prostate of the first patient in accordance with an illustrative embodiment.
Figure 4A:
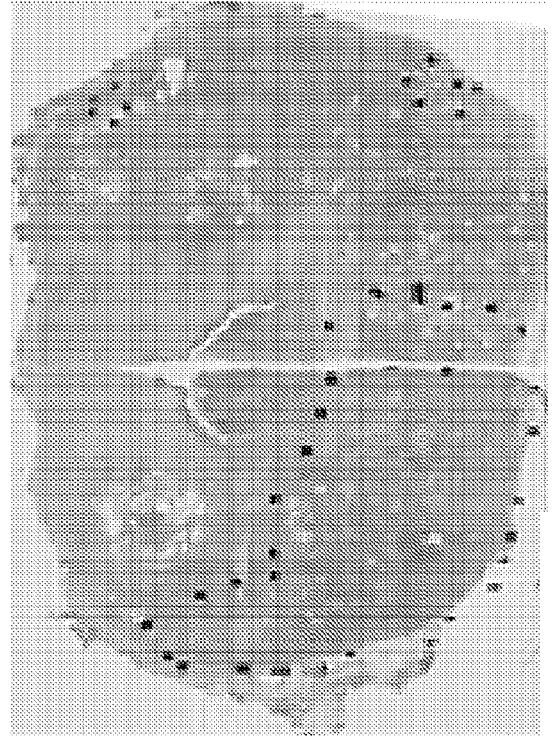

The inventors have conducted testing on a number of patients using the techniques described herein. As discussed in more detail below, the testing validates the efficacy of the proposed techniques. FIG. 4 depicts testing data and other results of a 4 quadrant analysis performed on a first patient, who is 60 years old. As depicted in the images, the first patient has a Gleason score 4+5 cancer in the right peripheral zone (PZ) of the prostate (outlined). FIG. 4A depicts a histological view of the prostate of the first patient in accordance with an illustrative embodiment. FIG. 4B depicts a T2-weighted MRI image of the prostate of the first patient in accordance with an illustrative embodiment. FIG. 4C is an ADC map that includes a marked region of interest (ROI) of the prostate in accordance with an illustrative embodiment.

Figure 4D:
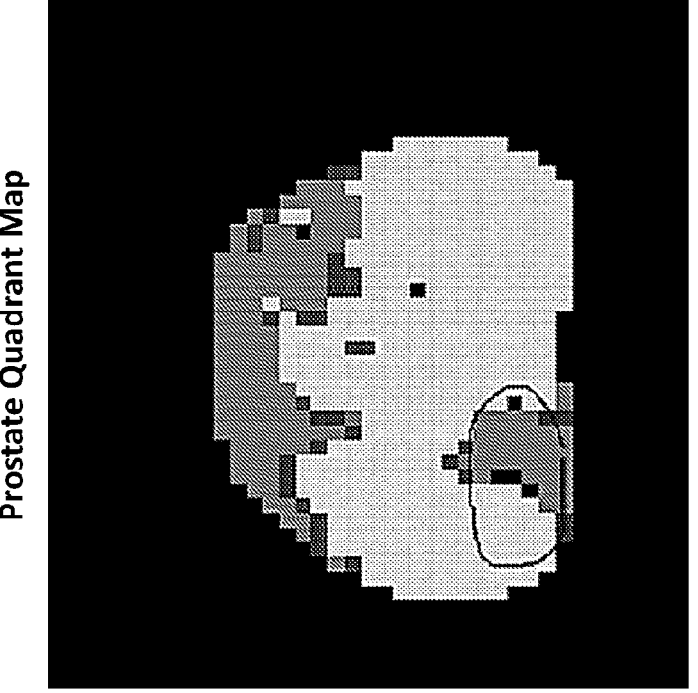
FIG. 4D is an HM-MRI quadrant map of the prostate in accordance with an illustrative embodiment.
Figure 4C:
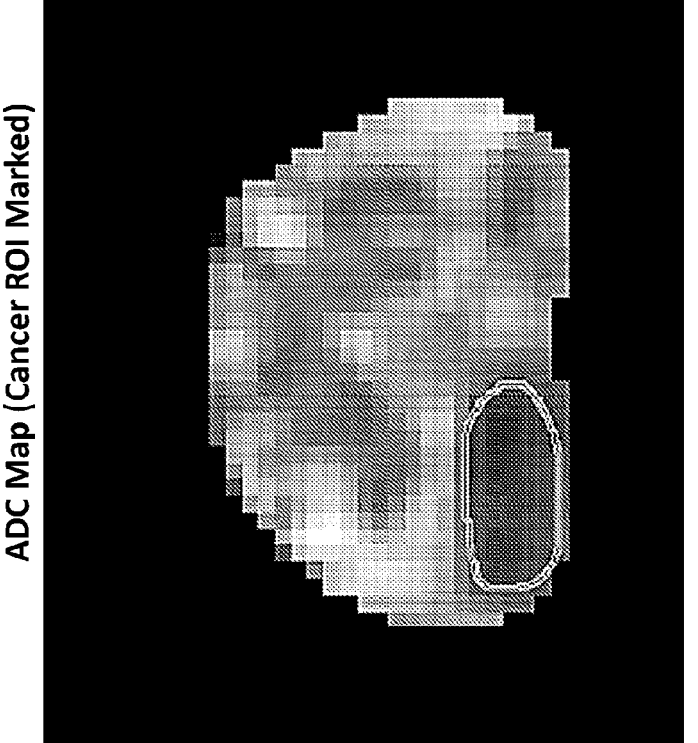
FIG. 4C is an ADC map that includes a marked region of interest (ROI) of the prostate in accordance with an illustrative embodiment.
Figures 4E, 4F:
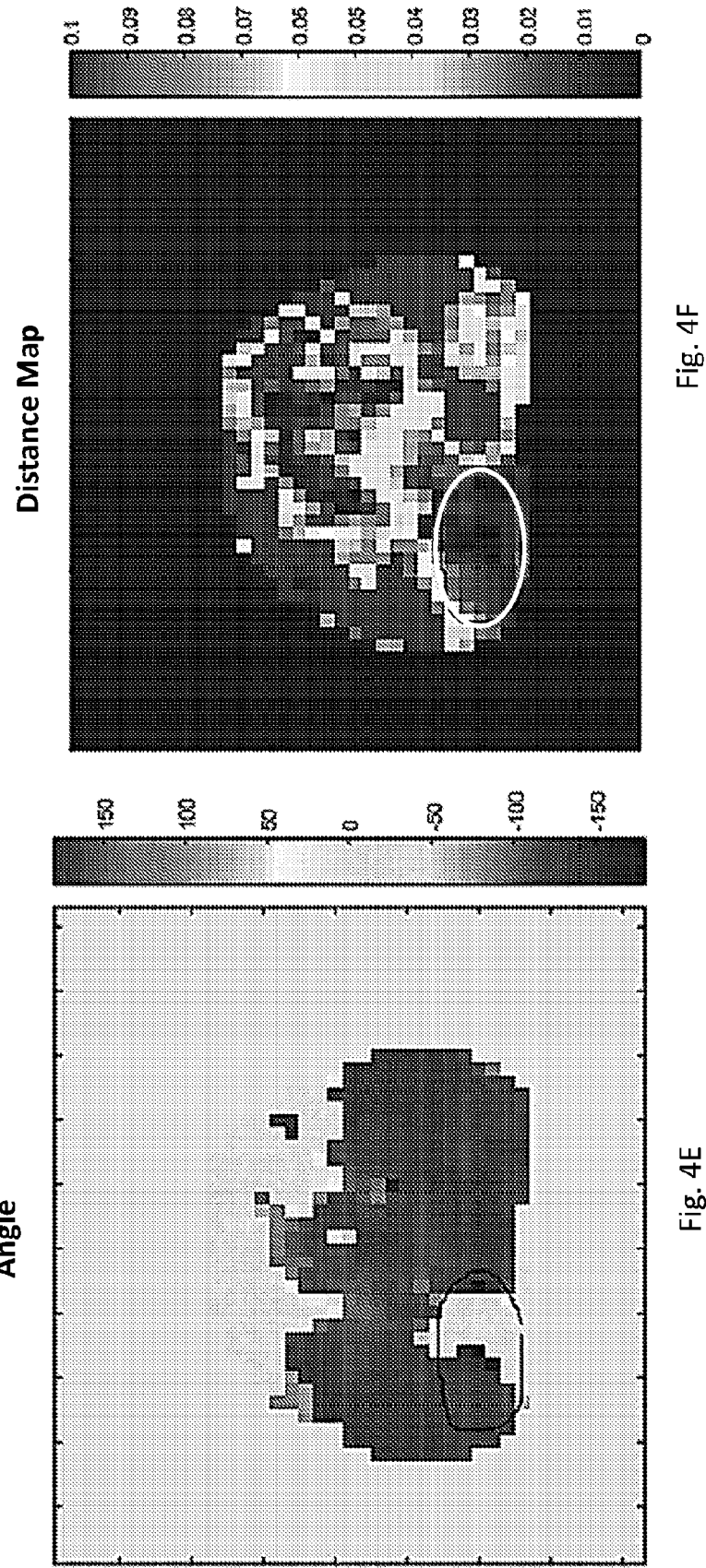
FIG. 4E is a quadrant map of the prostate depicting angle values in accordance with an illustrative embodiment.
FIG. 4F is a quadrant map of the prostate depicting distance values in accordance with an illustrative embodiment.

FIGS. 4D-4F depict various quadrant analysis parameter maps associated with the first patient. Specifically, FIG. 4D is an HM-MRI quadrant map of the prostate in accordance with an illustrative embodiment. FIG. 4E is a quadrant map of the prostate depicting angle values in accordance with an illustrative embodiment. FIG. 4F is a quadrant map of the prostate depicting distance values in accordance with an illustrative embodiment. Based on analysis of the test results from the first patient and others, it was determined that cancer is associated with higher prevalence of PQ4 voxels, lower angle (except anterior fibromuscular stroma (AFMS)), and lower distance from the origin. The cancer ROI shows that 2% of the voxels are from quadrant PQ1, 45% from quadrant PQ2, 6% from quadrant PQ3, and 47% from quadrant PQ4.

As discussed, the Quadrant maps of FIG. 4 show that the cancer appears different from the surrounding benign tissue (more PQ4). This is because the cancer has lower angle and distance measures compared to benign tissue. Preliminary results suggest that these four quadrant plots show cancers more clearly and have fewer false positives (e.g. in the TZ) compared to conventional ADC or T2. It also appears that benign prostatic hyperplasia (BPH) does not show up in 4QA, which indicates that the proposed techniques can be used to help differentiate BPH from cancer. However, it is also noted that the cancers are significantly smaller on 4QA than on ADC or T2. Anterior fibromuscular stroma (AFMS) remains a concern on the quadrant map, but as they have high distance (unlike cancer), they can be eliminated from consideration. A combination of distance and quadrant map, called the distance encoded quadrant map can also be used.

Figures 5A, 5B:
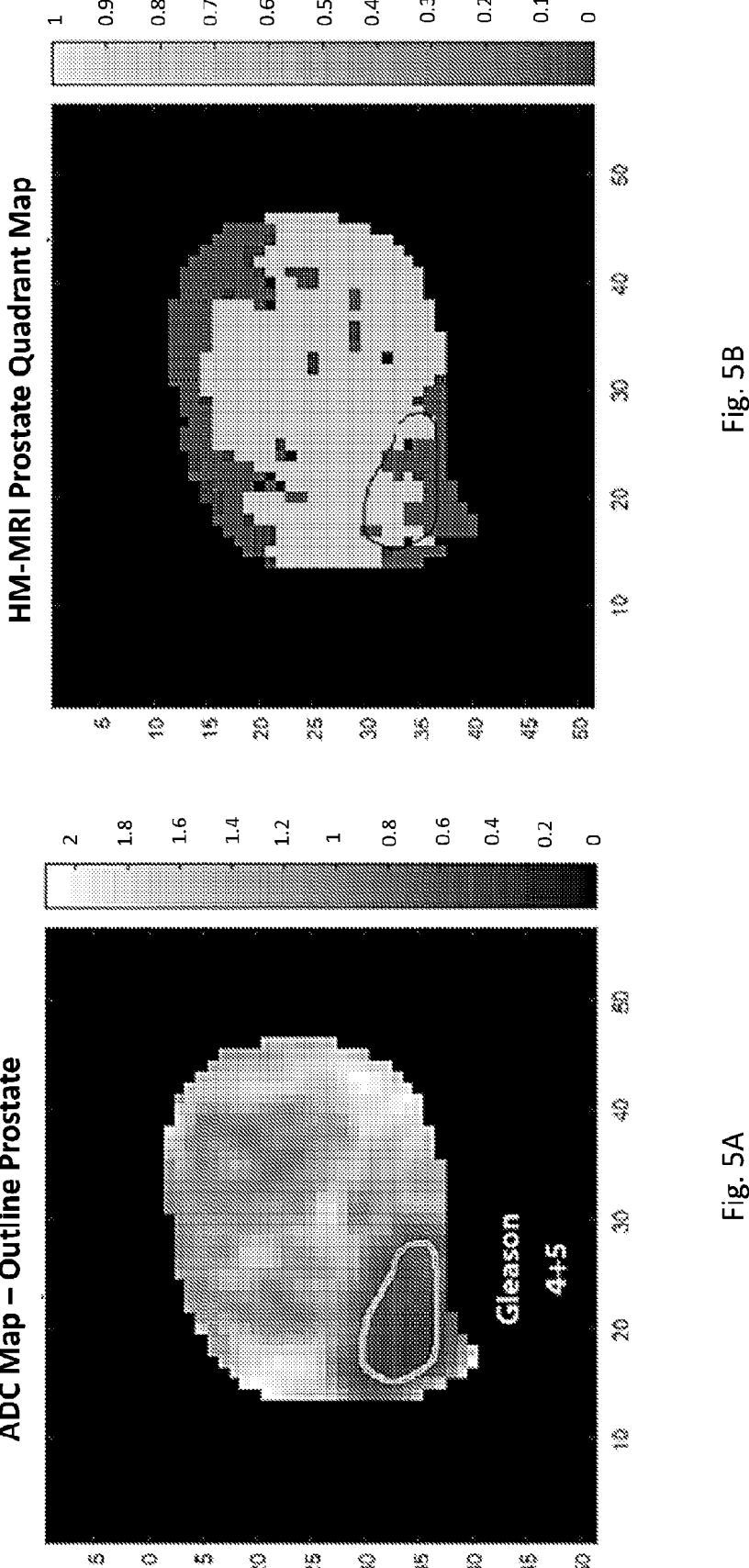
FIG. 5A depicts an ADC map with a marked ROI in the prostate in accordance with an illustrative embodiment.
FIG. 5B depicts an HM-MRI prostate quadrant map in accordance with an illustrative embodiment.
Figures 5C, 5D:
FIG. 5C is a quadrant map of the prostate depicting angle values in accordance with an illustrative embodiment.
FIG. 5D is a quadrant map of the prostate depicting distance values in accordance with an illustrative embodiment.

FIG. 5 is another representative example of four quadrant mapping and associated metrics in a 56 years old patient with Gleason 4+5 cancer in the right peripheral zone in mid prostate. FIG. 5A depicts an ADC map with a marked ROI in the prostate in accordance with an illustrative embodiment. FIG. 5B depicts an HM-MRI prostate quadrant map in accordance with an illustrative embodiment. FIG. 5C is a quadrant map of the prostate depicting angle values in accordance with an illustrative embodiment. FIG. 5D is a quadrant map of the prostate depicting distance values in accordance with an illustrative embodiment. As shown, cancer is associated with higher prevalence of PQ4 voxels, lower angle (except AFMS), and lower distance from origin. The cancer ROI shows that 2% of the voxels are from quadrant PQ1, 57% from quadrant PQ2, 3% from quadrant PQ3, and 38% from quadrant PQ4.

Figure 6C:
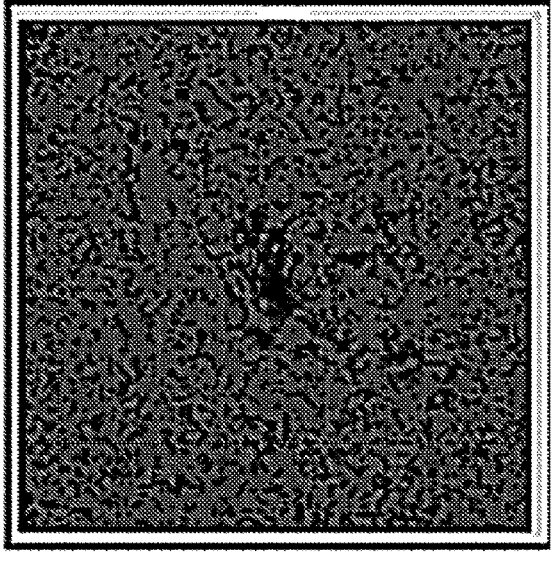
FIG. 6C depicts a third Eigenvalue (Eigenvalue 3; Blue) map calculated using the proposed matrix analysis technique for MRI data in accordance with an illustrative embodiment.
Figure 6B:
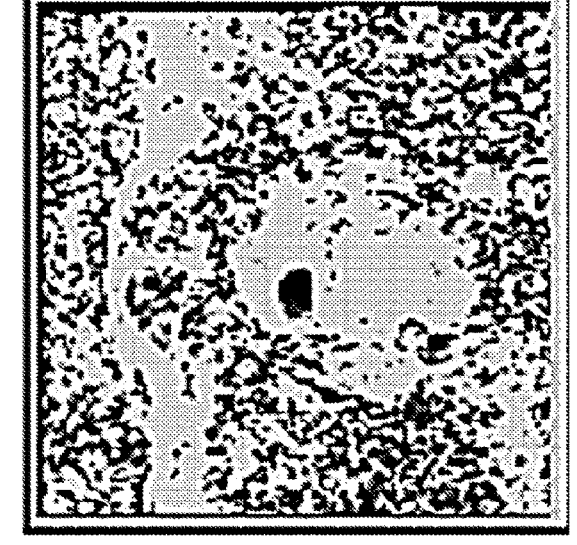
FIG. 6B depicts a second Eigenvalue (Eigenvalue 2; Green) map calculated using the proposed matrix analysis technique for MRI data in accordance with an illustrative embodiment.
Figure 6A:
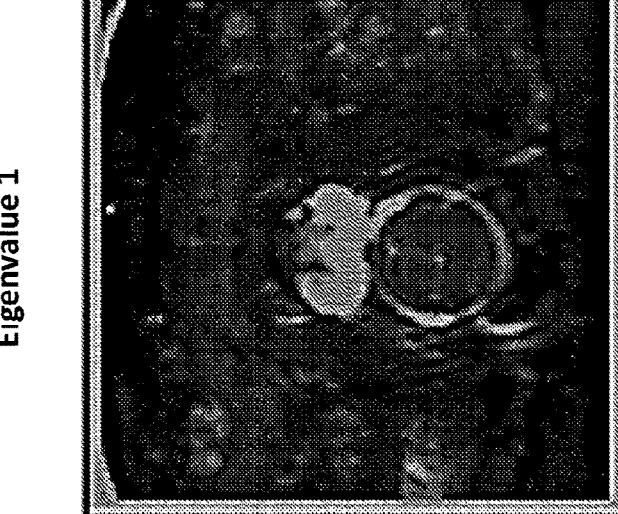
FIG. 6A depicts a first Eigenvalue (Eigenvalue 1; Red) map calculated using the proposed matrix analysis technique for MRI data in accordance with an illustrative embodiment.
Figure 6F:
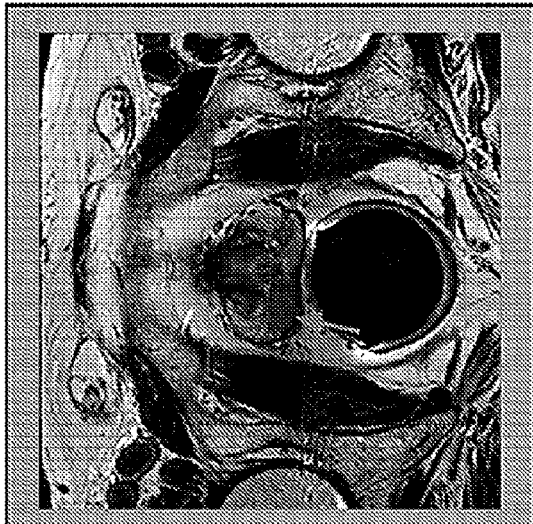
FIG. 6F is a T2-weighted view of the prostate corresponding to the combined Eigenvalue map of FIG. 6D in accordance with an illustrative embodiment.
Figure 6E:
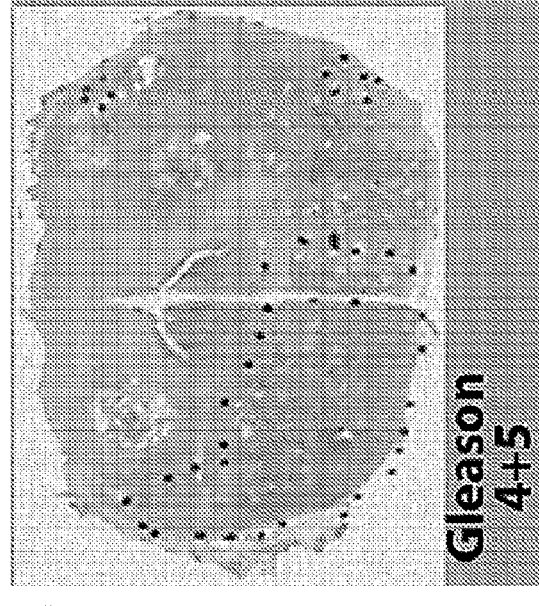
FIG. 6E is a histological view of the prostate corresponding to the combined Eigenvalue map of FIG. 6D in accordance with an illustrative embodiment.
Figure 6D:
FIG. 6D depicts a combined Eigenvalue map in accordance with an illustrative embodiment.
Figure 6D:
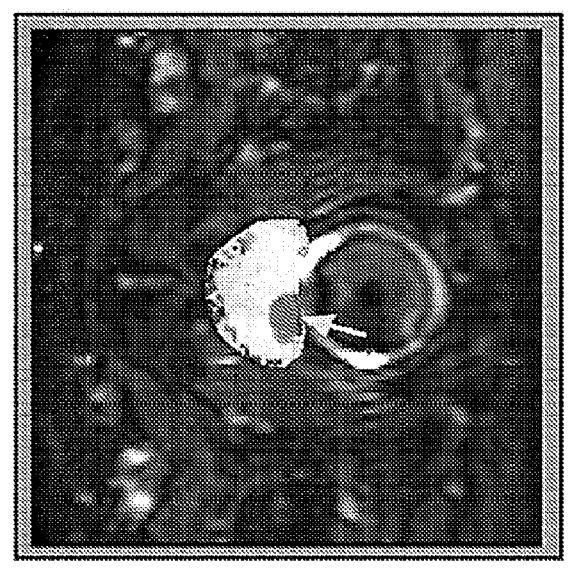

A matrix analysis was also implemented, and it was determined that the combination of three eigenvalues was effective in the differentiation of prostate cancer from benign tissue. In alternative embodiments, a different number of Eigenvalues may be used, such as (4, 5, 6, etc.). FIG. 6 depicts a matrix analysis performed for a 60 year old patient. FIG. 6A depicts a first Eigenvalue (Eigenvalue 1; Red) map calculated using the proposed matrix analysis technique for MRI data in accordance with an illustrative embodiment. FIG. 6B depicts a second Eigenvalue (Eigenvalue 2; Green) map calculated using the proposed matrix analysis technique for MRI data in accordance with an illustrative embodiment. FIG. 6C depicts a third Eigenvalue (Eigenvalue 3; Blue) map calculated using the proposed matrix analysis technique for MRI data in accordance with an illustrative embodiment. FIG. 6D depicts a combined Eigenvalue map in accordance with an illustrative embodiment. FIG. 6E is a histological view of the prostate corresponding to the combined Eigenvalue map of FIG. 6D in accordance with an illustrative embodiment. FIG. 6F is a T2-weighted view of the prostate corresponding to the combined Eigenvalue map of FIG. 6D in accordance with an illustrative embodiment.

As shown, the region in the right posterolateral peripheral zone (dark region indicated by arrow) highlights cancer in the combined Eigenvalue map of FIG. 6D. This matches with the presences of Gleason 4+5 cancer (arrow) on whole-mount histology from a prostatectomy specimen (FIG. E) and on the corresponding T2-weighted high resolution image (FIG. F). Using a simplified version of the matrix analysis on the same patients, the measured matrix analysis metrics performed well in the differentiation of prostate cancer from normal prostate with an area under the ROC curve=0.95-0.96.

FIG. 7 depicts textual results of the tests and analysis conducted to demonstrate the methods and systems described herein. FIG. 7A is a table that includes a summary of measured metrics across prostate cancer, the benign peripheral zone, the benign transition zone, the benign central zone, and anterior fibromuscular stroma in accordance with an illustrative embodiment. The measured metrics include analysis of variance (ANOVA) data and Tukey's honestly significant difference (HSD) test data. FIG. 7B is a table that includes a summary of measured metrics for Gleason score 6 cancer, Gleason score 7 cancer, and Gleason score 9 cancer, along with the Spearman correlation coefficients in accordance with an illustrative embodiment.

Figure 7D:
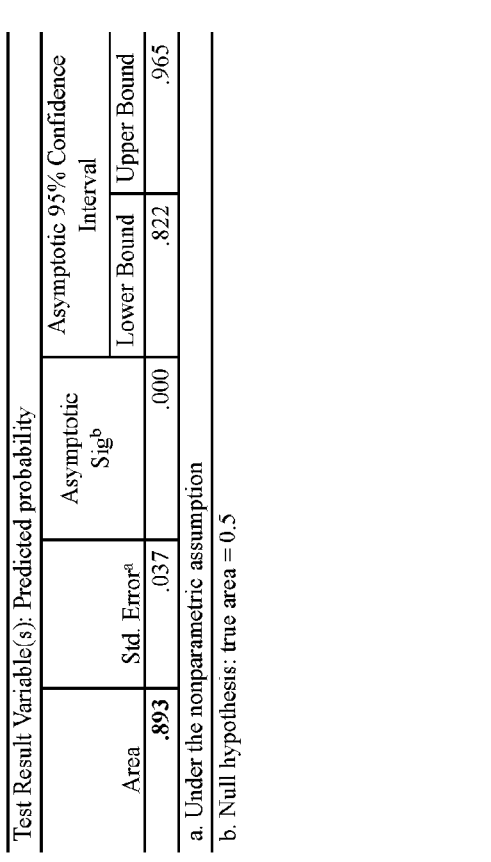
FIG. 7D is a table that shows area under the curve in accordance with an illustrative embodiment.
Figure 7C:
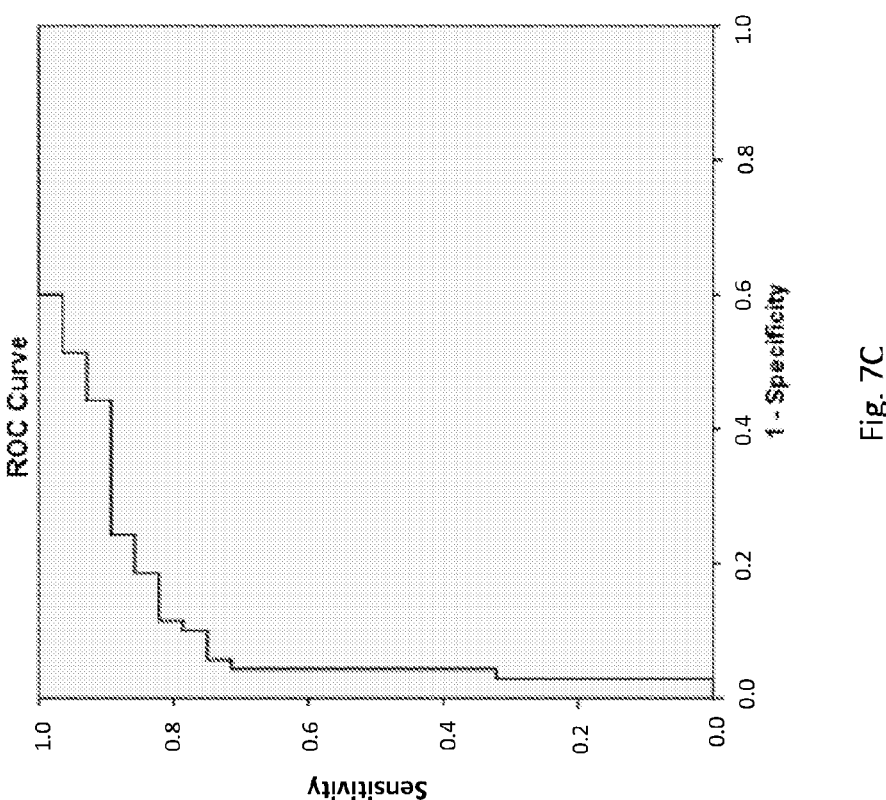
FIG. 7C depicts a receiver operating characteristic (ROC) curve for the diagnosis of prostate cancer using four quadrant analysis in 20 patients in accordance with an illustrative embodiment.

FIG. 7C depicts a receiver operating characteristic (ROC) curve for the diagnosis of prostate cancer using four quadrant analysis in 20 patients in accordance with an illustrative embodiment. FIG. 7D is a table that shows area under the curve in accordance with an illustrative embodiment. The combination of four quadrant analysis metrics showed an area under the curve (AUC) of 0.893 (standard error 0.037, 95% confidence interval [0.822, 0.965], $p<0.05$) for the differentiation of prostate cancer from benign prostatic tissue. This diagnostic performance is better than that shown by visual assessment of mpMRI by radiologists (metadata study shows AUC~0.78).

Thus, using the proposed systems and methods to obtain complementary information from four quadrant analysis and matrix analysis in the diagnosis of cancer can be very effective. These techniques can be used either by themselves or together for the diagnosis of cancer and other applications. As discussed, the proposed systems and methods differ substantially from existing techniques. For example, unlike traditional techniques, the proposed four quadrant analysis analyzes data on a voxel-by-voxel basis. The representation of this data using a vector for each pixel provides both amplitude and angle information for each individual pixel. Additionally, in some embodiments, a color-coded representation of the data is presented as vectors in the 4-quadrant space. Alternatively, instead of color coding, a different visualization tool may be used, such as text markers, patterns, symbols, etc. Also, instead of considering only 2 data points as was done in prior techniques, the proposed four quadrant analysis utilizes the entire sampled dataset, using slope of calculated ADC vs. 'TE' value, and the slope of calculated T2 vs. 'b' value. This can be implemented in any type of hybrid matrix 2×2, 3×3, 3×4, 4×4, etc. (i.e. any combination of 'b' and 'TE' values).

The proposed application of matrix analysis to medical imaging data is also different from traditional techniques. Previous MRI studies have used matrix analysis for diffusion tensor imaging (DTI), longitudinal and transverse relaxations in the rotating frame, and functional magnetic resonance imaging (FMRI). For example, DTI studies use the eigenvalue as the magnitude of the diffusion along the direction of the eigenvector. Fractional anisotropy or the amount of diffusion asymmetry is used to characterize underlying tissue microstructure. However, no prior studies have used matrix analysis to extract diagnostic information from measurements of ADC as a function of TE, and T2 and a function of b, as described herein. The matrices produced by the hybrid multidimensional MRI approach are very different from other matrix representations of MRI data, and the application of matrix analysis to this data produces new and interesting results. As discussed, in one embodiment, the proposed system determines the eigenvalues of the hybrid matrix associated with each image voxel. Each of the eigenvalues and also linear combinations of the eigenvalues are mapped, and this information is used to identify cancers.

Some applications of the proposed methods and systems include modification of risk maps based on 4QA (e.g., modify probabilities on standard risk maps based on whether pixels are near regions identified by 4QA as probably high grade cancers). In such an embodiment, weights assigned to low ADC or T2, and high dynamic contrast enhanced (DCE) alpha in nearby pixels can be increased to get more accurate risk maps. They can also be added to tissue composition estimates from HM-MRI to improve the risk diagnosis and improve the differentiation of clinically significant cancers from non-significant cancers.

The proposed methods and systems can also be used for targeted biopsy. For example, 4QA can be used to guide biopsy to the most aggressive area(s) of cancer. The data demonstrates that 4QA identifies aggressive cancers, and use of 4QA would thus be an important way to make biopsy more sensitive, which will reduce false negatives. The 4QA techniques can also be used to find and follow benign prostatic hyperplasia (BPH) (e.g., to assess severity and monitor response to therapy). Regions in the transitional zone (TZ) that show up with low ADC (or potentially high DCE alpha) but don't show up on 4QA (either 4QM, angle, or distance maps) are more likely to be BPH rather than cancer. The system could thus be used to reliably show BPH.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A diagnostic system to analyze imaging data comprising:
a memory configured to store hybrid imaging data of a tissue sample; and
a processor operatively coupled to the memory and configured to:
generate a four quadrant plot based on the hybrid imaging data, wherein each point in the four quadrant plot corresponds to an image voxel of the tissue sample;
generate, based on the hybrid imaging data, a matrix of b-values and echo time (TE) values for each image voxel in the four quadrant plot;
determine, by the processor, a change in apparent diffusion coefficient (ADC) as a function of TE and a change in T2 as a function of b-value based on the matrix;
identify, by the processor and based on the matrix, a plurality of eigenvalues for each image voxel; and
determine, by the processor and based at least in part on the plurality of eigenvalues, whether each image voxel of the tissue sample is associated with cancerous tissue or non-cancerous tissue.

2. The system of claim 1, further comprising a magnetic resonance imaging system configured to generate the hybrid imaging data, wherein the hybrid imaging data includes both T2-weighted imaging data and diffusion-weighted imaging data corresponding to the tissue sample.

3. The system of claim 1, wherein the matrix comprises a 3×3 matrix.

4. The system of claim 1, wherein a y-coordinate is equal to a slope of apparent diffusion coefficient (ADC) as a function of TE in the four quadrant plot.

5. The system of claim 1, wherein an x-coordinate is equal to a slope of T2 as a function of b-value in the four quadrant plot.

6. The system of claim 1, wherein the processor determines one or more distance values that comprise absolute distances from an origin of the four quadrant plot to the image voxels.

7. The system of claim 6, wherein the processor determines one or more angle values for each of the image voxels, wherein the one or more angles values are relative to the origin of the four quadrant plot.

8. The system of claim 1, wherein the processor is further configured to generate one or more hybrid matrix analysis parameter plots based on the hybrid imaging data, wherein the one or more hybrid matrix parameter plots include the plurality of eigenvalues.

9. The system of claim 8, wherein the processor is configured to combine the plurality of eigenvalues and to map a combination of the plurality of eigenvalues to identify one or more characteristics of the tissue sample.

10. The system of claim 1, wherein determination of whether each image voxel of the tissue sample is associated with the cancerous tissue or the non-cancerous tissue is based at least in part on which quadrant the image voxels are positioned.

11. A diagnostic method of analyzing imaging data, the method comprising:
storing, in a memory of a computing system, hybrid imaging data of a tissue sample; and
generating, by a processor operatively coupled to the memory, a four quadrant plot based on the hybrid imaging data, wherein each point in the four quadrant plot corresponds to an image voxel of the tissue sample;

generating, by the processor and based on the hybrid imaging data, a matrix of b-values and echo time (TE) values for each image voxel in the four quadrant plot;

determining, by the processor, a change in apparent diffusion coefficient (ADC) as a function of TE and a change in T2 as a function of b-value based on the matrix;

identifying, by the processor and based on the matrix, a plurality of eigenvalues for each image voxel; and determining, by the processor and based at least in part on the plurality of eigenvalues, whether each image voxel of the tissue sample is associated with cancerous tissue or non-cancerous tissue.

12. The method of claim 11, wherein y is equal to a slope of apparent diffusion coefficient (ADC) as a function of TE in the four quadrant plot, and x is equal to a slope of T2 as a function of b-value in the four quadrant plot.

13. The method of claim 11, wherein the matrix comprises a 3×3 matrix.

14. The method of claim 11, further comprising combining and mapping, by the processor, the plurality of eigenvalues, wherein determination of whether each image voxel of the tissue sample is associated with the cancerous tissue or non-cancerous tissue is based at least in part on the mapped combination of eigenvalues.

* * * * *